(12) United States Patent
Weitzner et al.

(10) Patent No.: US 9,549,716 B2
(45) Date of Patent: Jan. 24, 2017

(54) MEDICAL DEVICE CONTROL SYSTEM

(75) Inventors: Barry Weitzner, Acton, MA (US); John Golden, Norton, MA (US); Frank T. McDonald, Bedford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 387 days.

(21) Appl. No.: 12/567,256

(22) Filed: Sep. 25, 2009

(65) Prior Publication Data

US 2010/0114116 A1 May 6, 2010

Related U.S. Application Data

(63) Continuation of application No. 11/165,593, filed on Jun. 22, 2005, now Pat. No. 7,618,413.

(51) Int. Cl.
| | |
|---|---|
| *A61B 1/00* | (2006.01) |
| *A61B 10/06* | (2006.01) |
| *A61B 17/29* | (2006.01) |
| *A61M 25/01* | (2006.01) |
| *A61B 17/00* | (2006.01) |
| *A61B 10/02* | (2006.01) |

(52) U.S. Cl.
CPC ............ *A61B 10/06* (2013.01); *A61B 17/29* (2013.01); *A61B 17/2909* (2013.01); *A61M 25/0147* (2013.01); *A61B 34/70* (2016.02); *A61B 2010/0208* (2013.01); *A61B 2017/003* (2013.01); *A61B 2017/0042* (2013.01); *A61B 2017/00292* (2013.01); *A61B 2017/00367* (2013.01); *A61B 2017/00398* (2013.01); *A61B 2017/2912* (2013.01)

(58) Field of Classification Search
CPC .................. A61B 1/0052; A61B 2017/00318
USPC ............. 600/101, 104, 118, 146, 148, 149; 604/95.04, 523, 528; 606/1, 130, 523, 528
See application file for complete search history.

(56) References Cited

U.S. PATENT DOCUMENTS

| | | | |
|---|---|---|---|
| 3,485,234 A | 12/1969 | Stevens | |
| 3,949,757 A | 4/1976 | Sabel | |
| 4,499,895 A * | 2/1985 | Takayama | 600/148 |

(Continued)

FOREIGN PATENT DOCUMENTS

| | | |
|---|---|---|
| WO | WO 94/21179 A2 | 9/1994 |
| WO | WO 97/12557 A1 | 4/1997 |

(Continued)

OTHER PUBLICATIONS

International Search Report and Written Opinion issued in International Application No. PCT/US2006/024719 (Publication No. WO/2007/002545); Date of Mailing: Oct. 25, 2006.

(Continued)

*Primary Examiner* — Matthew J Kasztejna
*Assistant Examiner* — Rynae Boler
(74) *Attorney, Agent, or Firm* — Bookoff McAndrews, PLLC (57) ABSTRACT

A control system for allowing a physician to control the orientation of a medical device or a medical instrument in a variety of directions with one hand. An actuator selectively tensions one or more control cables having ends secured at or adjacent a distal tip of the medical device in order to bend the distal tip in a desired direction. In one embodiment, a physician can adjust the movement of the distal tip in a desired direction without affecting the orientation of the medical device in other directions.

27 Claims, 5 Drawing Sheets

(56) References Cited

U.S. PATENT DOCUMENTS

| | | | |
|---|---|---|---|
| 4,503,842 A * | 3/1985 | Takayama | 600/152 |
| 4,539,976 A | 9/1985 | Sharpe | |
| 4,826,087 A | 5/1989 | Chinery | |
| 5,025,778 A | 6/1991 | Silverstein et al. | |
| 5,120,323 A | 6/1992 | Shockey et al. | |
| 5,159,446 A * | 10/1992 | Hibino et al. | 348/65 |
| 5,254,088 A | 10/1993 | Lundquist et al. | |
| 5,284,130 A * | 2/1994 | Ratliff | 600/229 |
| 5,325,845 A | 7/1994 | Adair | |
| 5,402,793 A * | 4/1995 | Gruner et al. | 600/447 |
| 5,423,848 A | 6/1995 | Washizuka et al. | |
| 5,462,527 A * | 10/1995 | Stevens-Wright et al. | 604/528 |
| 5,501,654 A | 3/1996 | Failla et al. | |
| 5,575,755 A * | 11/1996 | Krauter et al. | 600/148 |
| 5,643,294 A | 7/1997 | Tovey et al. | |
| 5,749,828 A | 5/1998 | Solomon et al. | |
| 5,813,813 A | 9/1998 | Daum et al. | |
| 5,827,323 A | 10/1998 | Klieman et al. | |
| 5,916,146 A | 6/1999 | Allotta et al. | |
| 5,931,849 A | 8/1999 | Desvignes et al. | |
| 5,976,121 A | 11/1999 | Matern et al. | |
| 5,984,939 A | 11/1999 | Yoon | |
| 6,001,114 A | 12/1999 | Ouchi | |
| 6,007,482 A | 12/1999 | Madni et al. | |
| 6,013,024 A | 1/2000 | Mitsuda et al. | |
| 6,017,322 A | 1/2000 | Snoke et al. | |
| 6,033,378 A | 3/2000 | Lundquist et al. | |
| 6,066,090 A | 5/2000 | Yoon | |
| 6,093,195 A | 7/2000 | Ouchi | |
| 6,126,665 A | 10/2000 | Yoon | |
| 6,156,027 A | 12/2000 | West | |
| 6,325,808 B1 | 12/2001 | Bernard et al. | |
| 6,352,503 B1 | 3/2002 | Matsui et al. | |
| 6,451,027 B1 * | 9/2002 | Cooper et al. | 606/130 |
| 6,527,753 B2 | 3/2003 | Sekine et al. | |
| 6,551,237 B2 | 4/2003 | Matsui | |
| 6,648,816 B2 | 11/2003 | Irion et al. | |
| 6,656,111 B2 * | 12/2003 | Fujii | A61B 1/0052 600/139 |
| 6,755,812 B2 | 6/2004 | Peterson et al. | |
| 6,793,622 B2 | 9/2004 | Konomura et al. | |
| 6,837,849 B2 | 1/2005 | Ogura et al. | |
| 6,858,024 B1 | 2/2005 | Berg et al. | |
| 6,899,673 B2 * | 5/2005 | Ogura | A61B 1/0051 600/139 |
| 6,991,602 B2 | 1/2006 | Nakazawa et al. | |
| 7,029,435 B2 | 4/2006 | Nakao | |
| 7,090,683 B2 | 8/2006 | Brock et al. | |
| 7,153,314 B2 | 12/2006 | Laufer et al. | |
| 7,156,857 B2 | 1/2007 | Pasricha et al. | |
| 7,199,790 B2 | 4/2007 | Rosenberg et al. | |
| 7,338,505 B2 | 3/2008 | Belson | |
| 7,410,483 B2 | 8/2008 | Danitz et al. | |
| 7,537,550 B1 | 5/2009 | Krull | |
| 7,608,083 B2 | 10/2009 | Lee et al. | |
| 2001/0049497 A1 | 12/2001 | Kalloo et al. | |
| 2002/0068868 A1 | 6/2002 | Thompson et al. | |
| 2002/0087048 A1 | 7/2002 | Brock et al. | |
| 2002/0165430 A1 | 11/2002 | Matsui | |
| 2003/0004460 A1 | 1/2003 | Bedell | |
| 2003/0018237 A1 | 1/2003 | Okada | |
| 2003/0050649 A1 | 3/2003 | Brock et al. | |
| 2003/0092965 A1 * | 5/2003 | Konomura et al. | 600/146 |
| 2003/0135204 A1 | 7/2003 | Lee et al. | |
| 2004/0019359 A1 | 1/2004 | Worley et al. | |
| 2004/0059191 A1 * | 3/2004 | Krupa et al. | 600/146 |
| 2004/0092794 A1 * | 5/2004 | Chin et al. | 600/146 |
| 2004/0097789 A1 * | 5/2004 | Weinberg | A61B 1/31 600/160 |
| 2004/0138525 A1 | 7/2004 | Saadat et al. | |
| 2004/0181140 A1 | 9/2004 | Falwell et al. | |
| 2004/0193016 A1 * | 9/2004 | Root et al. | 600/146 |
| 2004/0236316 A1 | 11/2004 | Danitz et al. | |
| 2004/0260245 A1 | 12/2004 | Clem et al. | |
| 2004/0267093 A1 | 12/2004 | Miyagi et al. | |
| 2005/0033355 A1 | 2/2005 | Frank et al. | |
| 2005/0054899 A1 | 3/2005 | Miyake | |
| 2005/0075538 A1 | 4/2005 | Banik et al. | |
| 2005/0096694 A1 | 5/2005 | Lee | |
| 2005/0117118 A1 * | 6/2005 | Miller et al. | 351/246 |
| 2005/0154261 A1 | 7/2005 | Ohline et al. | |
| 2005/0245789 A1 | 11/2005 | Smith et al. | |
| 2005/0251091 A1 | 11/2005 | Saadat et al. | |
| 2005/0277945 A1 | 12/2005 | Saadat et al. | |
| 2005/0288549 A1 | 12/2005 | Mathis | |
| 2006/0007184 A1 | 1/2006 | Rosenberg et al. | |
| 2006/0020287 A1 | 1/2006 | Lee et al. | |
| 2006/0079873 A1 | 4/2006 | Scopton et al. | |
| 2006/0089626 A1 | 4/2006 | Vlegele et al. | |
| 2006/0178560 A1 | 8/2006 | Saadat et al. | |
| 2006/0178562 A1 | 8/2006 | Saadat et al. | |
| 2006/0264705 A1 | 11/2006 | Adams et al. | |
| 2007/0049435 A1 | 3/2007 | Jinno et al. | |
| 2007/0088340 A1 | 4/2007 | Brock et al. | |
| 2007/0100254 A1 | 5/2007 | Murakami et al. | |
| 2007/0135803 A1 | 6/2007 | Belson | |
| 2007/0167679 A1 | 7/2007 | Miyamoto et al. | |
| 2007/0167680 A1 | 7/2007 | Miyamoto et al. | |
| 2007/0219411 A1 | 9/2007 | Dejima et al. | |
| 2007/0249896 A1 | 10/2007 | Goldfarb et al. | |
| 2007/0249897 A1 | 10/2007 | Miyamoto et al. | |
| 2007/0255100 A1 | 11/2007 | Barlow et al. | |
| 2007/0255291 A1 * | 11/2007 | Brock et al. | 606/130 |
| 2008/0051629 A1 | 2/2008 | Sugiyama et al. | |
| 2008/0051631 A1 | 2/2008 | Dejima et al. | |
| 2008/0172029 A1 | 7/2008 | Dollar et al. | |
| 2008/0188868 A1 | 8/2008 | Weitzner et al. | |
| 2008/0188869 A1 | 8/2008 | Weitzner et al. | |
| 2008/0188871 A1 | 8/2008 | Smith et al. | |
| 2008/0188890 A1 | 8/2008 | Weitzner et al. | |
| 2008/0221391 A1 | 9/2008 | Weitzner et al. | |
| 2008/0243176 A1 | 10/2008 | Weitzner et al. | |
| 2008/0287862 A1 | 11/2008 | Weitzner et al. | |

FOREIGN PATENT DOCUMENTS

| | | |
|---|---|---|
| WO | WO 97/32528 A1 | 9/1997 |
| WO | WO 02/07611 A2 | 1/2002 |
| WO | WO 2007/033379 A2 | 3/2007 |

OTHER PUBLICATIONS

International Search Report and Written Opinion issued in International Application No. PCT/US2008/050923 (Publication No. WO/2008/144077); Date of Mailing: Oct. 9, 2008.

International Search Report and Written Opinion issued in International Application No. PCT/US2007/086079 (Publication No. WO 2008/070556); Date of Mailing: May 9, 2008.

Office Action issued in U.S. Appl. No. 11/165,593; Mail Date: Apr. 29, 2008.

Office Action issued in U.S. Appl. No. 11/165,593; Mail Date: Jan. 23, 2009.

Office Action issued in U.S. Appl. No. 11/165,593, Notice of Allowance; Mail Date: Jun. 29, 2009.

* cited by examiner

MEDICAL DEVICE CONTROL SYSTEM

This is a continuation of application Ser. No. 11/165,593, filed Jun. 22, 2005 now U.S. Pat. No. 7,618,413, which is incorporated herein by reference.

FIELD OF THE INVENTION

The present invention relates to medical devices in general, and in particular, to devices for manipulating steerable medical devices or other minimally invasive tools within a patient's body.

BACKGROUND OF THE INVENTION

Steerable medical devices and other minimally invasive surgical tools are being increasingly used to perform medical procedures inside a patient's body. Steerable devices generally include an elongated sheath and one or more control cables having distal ends secured at or adjacent the distal tip of the sheath. A control knob or lever selectively tightens the control cables in order to bend the device in a desired direction. The problem with most medical device controllers is that they require two hands in order to move the distal tip of a device in more than one plane. Alternatively, in those designs where a user can move the distal tip in four directions with one hand, two hands are still required in order to advance, retract, or rotate the device. Although some robotic systems have been proposed to allow a physician to direct a distal tip of a device in any direction using motors, these systems are generally expensive and complicated.

Given these problems, there is a need for a control system that allows a physician to manipulate a minimally invasive medical device in any desired direction with a single hand. In addition, the system should be low cost and easy to manufacture.

SUMMARY OF THE INVENTION

The present invention is a control system for selectively orienting the distal tip of a steerable medical device. In one embodiment, the control has a body with an actuator that can be independently moved in at least two directions so movement of the actuator in each direction moves the distal tip of the medical device in a plane. In one embodiment, the control may be mounted on a rail that is fixed with respect to the location of a patient such that advancement retraction of the control on the rail causes a corresponding advancement, retraction, or rotation of the medical device. In one particular embodiment, the actuator allows movement of the distal tip in one plane to be decoupled from movement in another plane.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
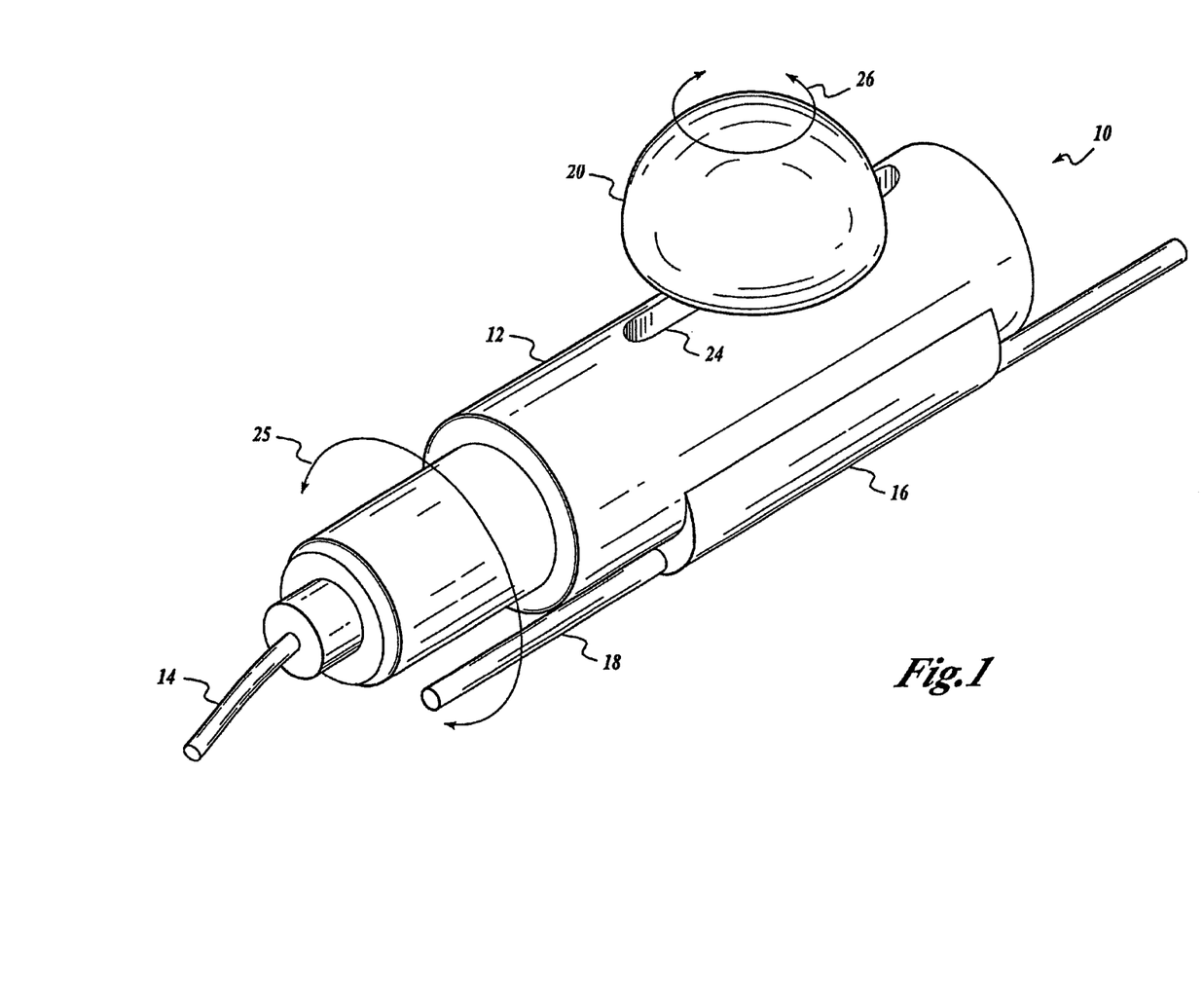
FIG. 1 is an elevated isometric view of a medical device control system in accordance with one embodiment of the present invention.

As indicated above, the present invention is a control system for selectively orienting a steerable medical device in a number of directions with one hand. In one embodiment of the invention, the control 10 includes a ergonomic, generally cylindrical body 12 having an actuator (described below) that operates to selectively tighten or release control cables that cause the distal tip of a medical device 14 such as a catheter, visualization device or instrument to bend in a desired direction. The body 12 includes one or more clamps 16 that allow it to be moved along a length of a rail 18 in order to advance or retract the medical device 14 as well as to provide rotation of the medical device around its longitudinal axis. The clamps 16 may provide a friction force that is overcome by a user in order to move the body 12 along the rail. Alternatively, the clamps 16 may include release mechanisms such as a brake or lock that should be unlocked to adjust the position of the body with respect to the rail 18. In yet another embodiment, the clamps 16 and rail 18 include a gear to move the body 18. The rail 18 may be clamped to a patient table or otherwise remain fixed with respect to the location of the patient such that the position of the medical device 14 remains constant if the physician's hand is removed from the control 10.

The control 10 can be rotated about the longitudinal axis of the rail 18 in the direction of the arrow 25 in order to impart rotational motion or torque to the medical device 14. Although the center axis of the medical device 14 is offset from the central axis of the rail 18, the medical device 14 is usually routed through a guiding device such as an endoscope or other constraining mechanism such that movement of the control 10 about the axis of the rail 18 causes the distal tip of the medical device 14 to rotate around the longitudinal axis of the device.

Finally, the control 10 includes an actuator 20 that is used by a physician, or their assistant, in order to move the distal tip of the medical device 14 in one or more of the up/down or right/left directions. In one embodiment, the actuator 20 can be moved forward or backward within a slot 24 that extends longitudinally along the top of the body 12 in order to move the distal tip of the medical device 14 up or down. In addition, the actuator 20 can be rotated as indicated by the arrow 26 in order to move the distal tip in the right/left direction. As will be explained in further detail below, movement of the distal tip in the up/down direction is decoupled from movement of the distal tip in the right/left direction so that a physician can maintain the orientation of the distal tip in the up/down direction while changing the right/left orientation or vice versa. Using the control 10, the physician is able to adjust the orientation of the distal tip with one hand, thereby allowing the physician to perform more intricate operations within the patient.

Figure 2:
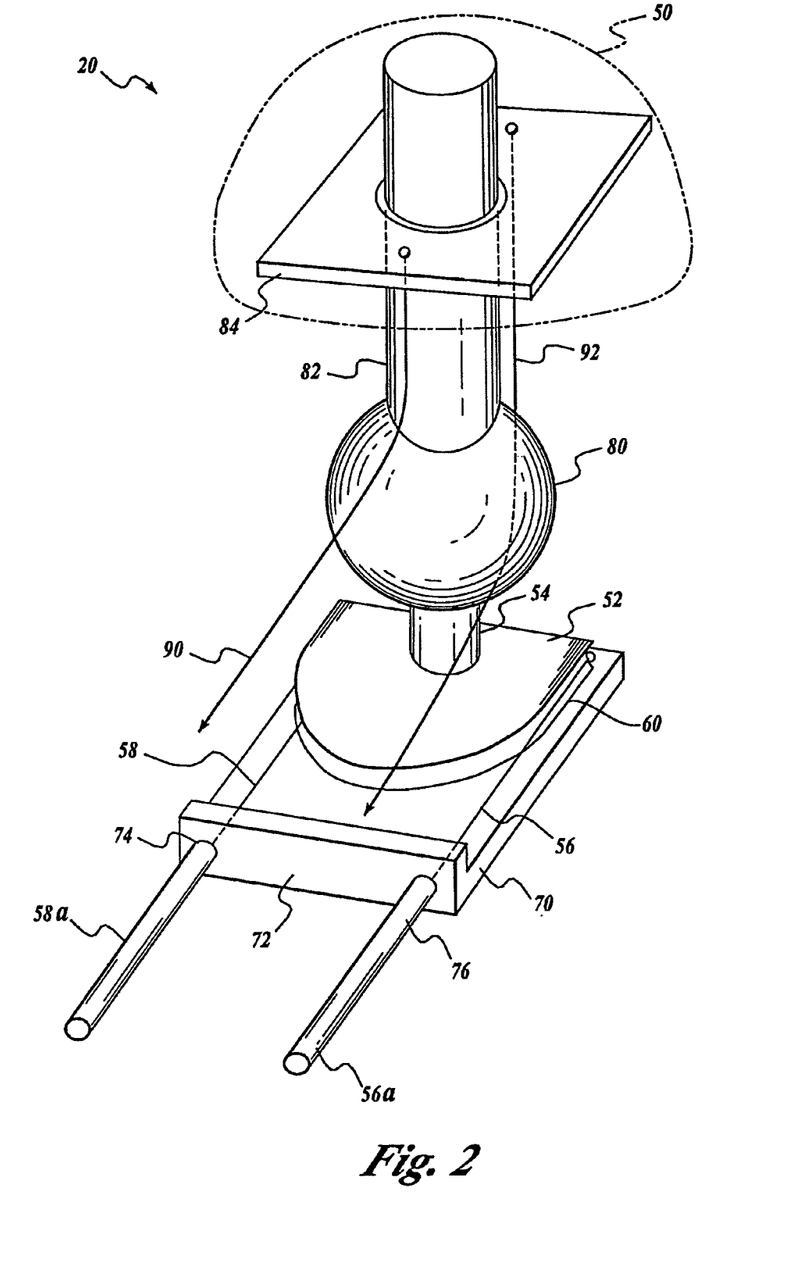
FIG. 2 illustrates one embodiment of an actuator for moving a medical device in accordance with the present invention.

As indicated above, the present invention allows an operator to adjust the orientation of a medical device with four degrees of freedom (up/down, left/right, forward/backward and rotationally) using one hand. FIG. 2 illustrates one embodiment of an actuator 20 for allowing a physician to change the up/down and right/left orientation of a distal tip of a medical device. The actuator 20 has a cap 50 that is connected to a cable guide plate 52 through a shaft 54. Rotation of the cap 50 about the longitudinal axis of the shaft 54 causes tension of one pair of control cables 56, 58. Tension of the control cable 56 causes a medical device tip to bend in the left direction, while tension on a control cable 58 causes a medical device tip to move in the rightward direction. The cable guide plate 52 is generally semi-circular in shape, with a rounded front end and a groove 60 therein to guide the corresponding control cables 56, 58. In the embodiment shown, the rear face of the cable guide plate 52 is generally flat. The ends of the control cables 56, 58 may be either fixedly secured to the cable guide plate 52 or slidably secured to the guide plate. If fixedly secured to the cable guide plate 52, then one control cable is tensioned while the other control cable is compressed as the cable guide plate is rotated by the cap 50. If the ends of the control cables are slidably secured to the cable guide plate, then one control cable is tensioned and the other is released from tension as the cable guide plate 52 is rotated. In some embodiments, the medical device 14 is permanently secured to the body 12 of the control. In other embodiments, the medical device is releasably secured to the body 12 by including cable connectors or the like that join the control cables in the medical device to the control cables in the body 12.

Also secured to the shaft 54 at a location adjacent the control cable guide plate 52 is a stop plate 70. The stop plate 70 has a raised lip 72 with a pair of holes 74, 76 therein through which the control cables 56, 58 are passed. Each of the control cables 56, 58 are preferably bowden cables, whereby the holes 74, 76 are sized such that the inner control cable of the bowden-type cables passes through the holes but the outer sheaths 56a, 56b of the bowden cables are too large to fit through the holes 74, 76. The stop plate 70 is shaped so that it does not rotate in the body of the control 10 when the actuator 20 is rotated around the axis of the shaft 54, but does move within the body of the control as the actuator is tilted back and forth. The stop plate 70 allows the physician to adjust the left/right position of the medical device 14 without adjusting the up/down position or vice-versa as will be explained below.

A ball joint 80 on the shaft 54 cooperates with a corresponding socket (not shown) in the interior of the body 12 of the control 10. A collar 82 is slidably mounted to the ball joint 80 and around the shaft 54. A top plate 84 is secured to the other end of the collar 82 and has a hole through which the shaft 54 is passed. The top plate secures the proximal ends of a pair of control cables 90, 92 that control the up/down movement of the medical device. The ball joint 80 allows the actuator 20 to be tilted back and forth with the interior of the body 12. Movement of the cap 50 towards the proximal end of the control 10 causes the control cable 90 to tighten, thereby causing the distal end of the medical device to move upwards. Similarly, pushing the cap 50 in the direction of the distal end of the control 10 causes the control cable 92 to tighten thereby causing the distal end of the medical device to move downwards.

Movement of the actuator 20 forwards and backwards about the axis of the ball joint 80 does not cause the distal tip of the medical device to move in the left/right direction. Similarly, rotation of the cap 50 about the longitudinal axis of the shaft 54 does not cause movement of the distal tip in the up/down direction. Therefore, the orientation of the medical device can be independently controlled in the up/down or right/left directions.

In some instances the control cables may be difficult to move with manual power alone. Therefore the actuator 20 may include a power assist mechanism to aid in tensioning the control cables. Such power assist may include hydraulic or pneumatic actuators, electric motors, magnets etc. that provide the additional force required to orient the distal tip of the medical device 14 in the desired direction.

Figures 3A, 3B:
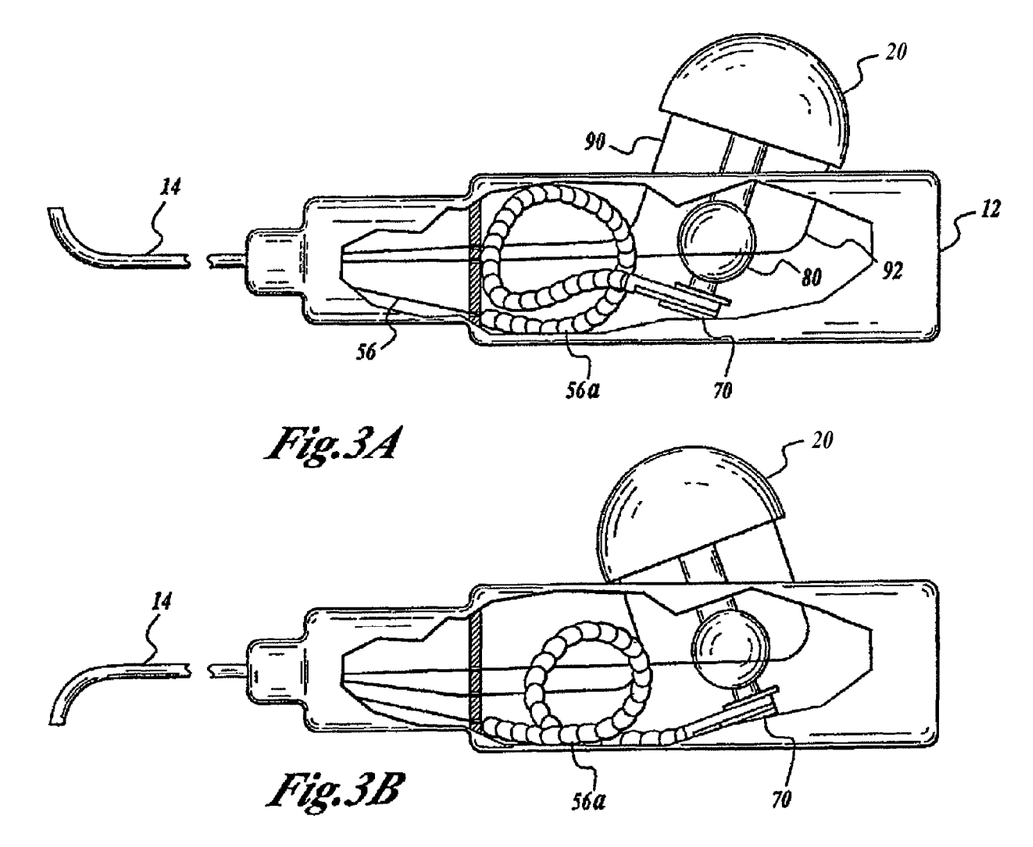
FIGS. 3A and 3B illustrate how an embodiment of the invention isolates movement of the distal tip of a controlled medical device.

FIGS. 3A and 3B illustrate how movement of the distal tip of the medical device 14 in the left/right direction is decoupled from movement of the medical device in the up/down direction. In the embodiment shown, the control cables 56, 58 controlling the left/right movement of the medical device 14 pass through the stop plate 70. Positioned over the control cables are the outer sheaths 56a, 58a of the bowden cables (see FIG. 2). The distal ends of the outer sheaths 56a, 58a are fixed with respect to the distal end of the medical device 14. The proximal ends of the outer sheaths 56a, 58a are joined to the stop plate 70 and move with the cable guide plate 52, as it is moved back and forth within the body 12. For example, control cable 56 has an outer sheath 56a having one end secured to the stop plate 70 and another end abutting the internal wall of the body 12, as shown in FIG. 3A. The outer sheath 56a is looped to have enough slack such that as the actuator 20 is tilted or moved, the slack in the outer sheath 56a is adjusted. As will be appreciated by those skilled in the art, the amount of bend imparted by the control cables 56, 58 to the distal tip of a medical device 14 depends upon the position of the ends of the control cables 56, 58 with respect to a proximal end of the outer sheaths 56a, 58a of the bowden cables. Because the outer sheaths include a loop or slack that allows them to move as the actuator 20 is moved, this distance does not change. Therefore, a user can adjust the up/down direction of the medical device 14 by tilting the actuator 20 forwards and backwards, as indicated in FIG. 3A and FIG. 3B, while not changing the orientation of the distal tip medical device in the left/right direction. In some cases, it may be desirable to limit the movement of the looped bowden cables to prevent them from becoming pinched. Therefore, the body 12 of the controller may include a slot or other restraint to limit the movement of the outer sheaths of the control cables to a single plane.

Although the presently disclosed embodiment of the invention operates the left/right direction by rotating the cap 50 around the axis of the shaft 54, it will be appreciated that the control cables could be arranged such that rotation of the cap causes the tip to move in the up/down direction and movement of the actuator 20 back and forth causes movement in the left/right direction. Alternatively, the actuator 20 could include nested, rotatable knobs to control both the up/down and left/right directions in a manner similar to that found in conventional endoscopes. If desired, the position of the medical device in the left/right direction can be fixed with brakes, mechanical stops, or a sufficient friction force on the cap 50 so that once the desired left/right position of the medical device is determined, the position of the medical device can remain fixed if the user releases the actuator. Alternatively, a braking force can be applied to the medical device control cables in order to fix the position of the medical device. Similarly, the position of the medical device in the up/down direction can be fixed by inhibiting movement of the actuator in the forward and reverse directions, or by applying a braking force to the control cables.

Figure 4:
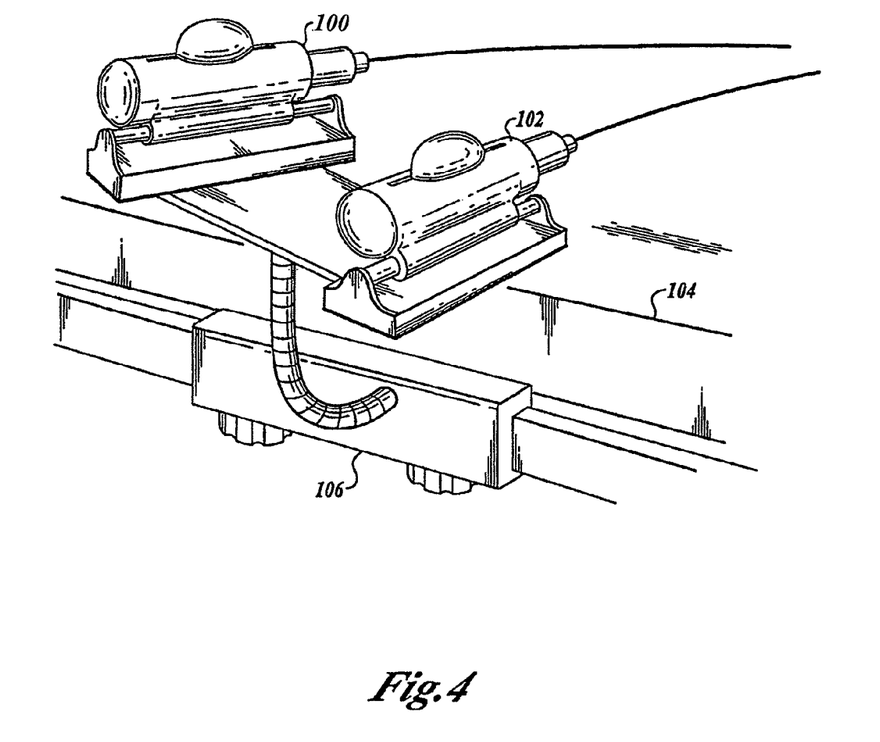
FIG. 4 illustrates how two control systems can be used by a physician.

FIG. 4 illustrates how a pair of controls 100, 102 can be secured at a fixed position with respect to a patient such as on a patient table 104 in order to allow a physician to control the orientation of a pair of medical devices. The medical devices preferably include one or more integrated instruments such as biopsy forceps, cauterizers, snares, scalpels, scissors, graspers, needle holders, staplers, fiber optic or solid state imagers etc. contained therein. Alternatively, the medical devices may be catheters that include or more lumens through which instruments can be routed. A moveable gooseneck 106 allows the position of the controls 100, 102 to be changed. Although the rails of the controls 100, 102 are shown connected to the gooseneck 106 with a pair of bases, it will be appreciated that the rails may be connected directly to a gooseneck or table 104, if desired. In yet another embodiment, one or more of the controls 100, 102 may be secured to the patient such as by strapping the controls to the patient's leg, torso, head etc. In other embodiments, the controls may be secured to the operator's body.

Figure 5:
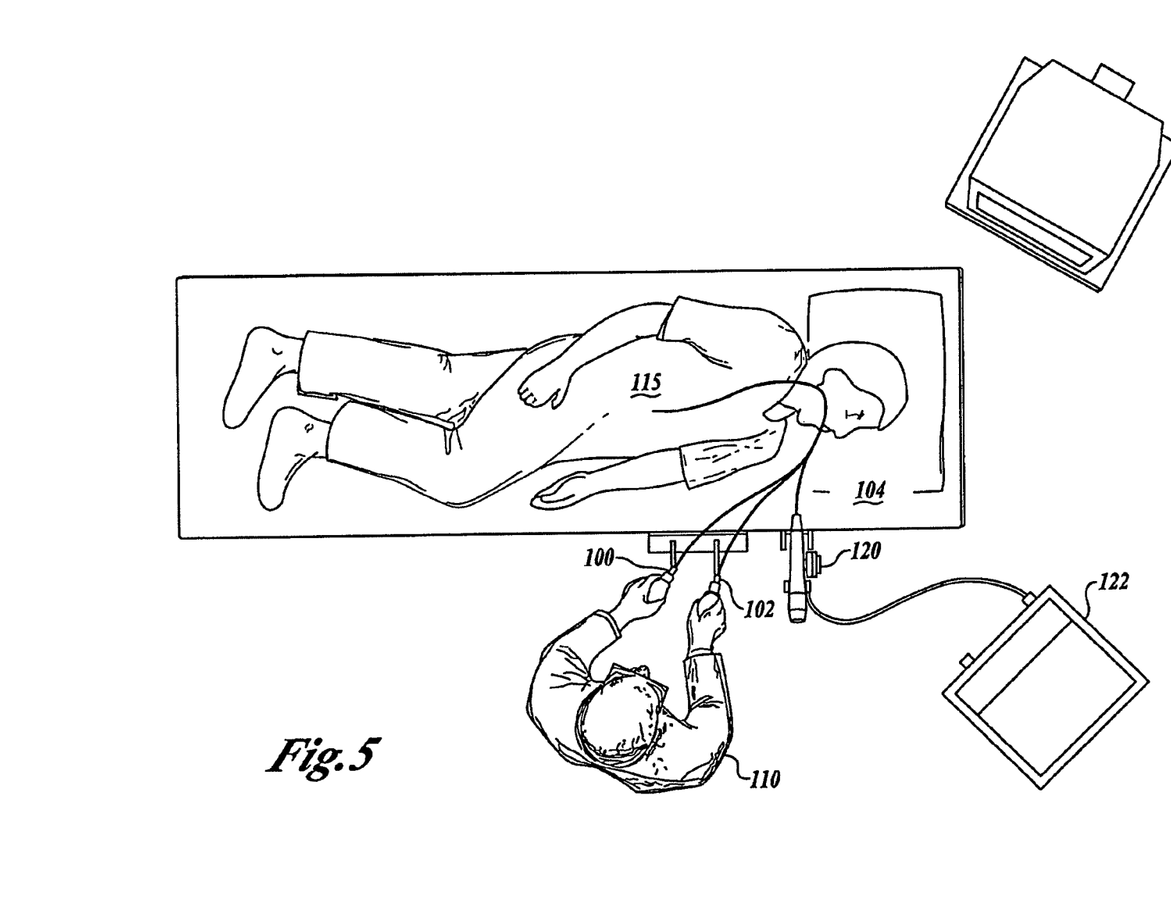
FIG. 5 illustrates how a physician operates a control system with each hand.

FIG. 5 illustrates how a physician 110 can use two hands to manipulate the pair of controls 100, 102 in order to perform a procedure within a patient 115. In practice, the medical devices controlled by the controls 100, 102 are often used in conjunction with a visualization device such as an endoscope 120 that produces images on a monitor 122 so that the physician can view the procedure. The present invention allows a physician to use two hands to control two medical devices in order to perform examinations or surgical procedures in the GI tract, colon, lungs, or through another orifice of the patient. Alternatively, the medical devices can be inserted through an incision such as with a trocar to access other areas of the body.

While the preferred embodiment of the invention has been illustrated and described, it will be appreciated that various changes can be made therein without departing from the scope of the invention. For example, additional actuator(s) could be included in the controls to tension/release control cables that terminate at other locations along the length of the medical device. For example, control cables may be secured to a location more proximal than the distal tip in order to provide bending at a more proximal portion of the device. These control cables can be tensioned with a second actuator on the control body. Alternatively, a single actuator can be used to tension more than one set of control cables. The actuator can selectively engage mechanisms to tension different control cables. Brakes or other devices can be used to fix the position of one set of control cables while the control cables from another set are adjusted. With a set of distal control cables and a set of proximal control cables, a tool in the medical device can have up to seven degrees of freedom (up/down, left/right at the distal end, up/down, left/right proximally, forward/backward, rotation about its axis and movement of the tool).

In some embodiments, movement of a medical device in the up/down, left/right direction may be controlled with actuators such as servo motors, hydraulic, pneumatic actuators disposed in a housing that is movable along and rotatable over a fixed rail in order to adjust the distal/proximal movement of a medical device as well as rotation of a device.

In addition, the controls may also include buttons, triggers or other actuators that activate particular tools such as forceps, snares, electrocauterizers, graspers, scissors, staplers etc. The actuators may be manually controlled or power assisted using pneumatics, hydraulics, motors, magnets etc. Therefore, the scope of the invention is to be determined from the following claims and equivalents thereto.

The embodiments of the invention in which an exclusive property or privilege is claimed are defined as follows:

1. A control for orienting a medical device having elongate control members operably associated with a distal tip of the medical device, the control comprising:
   a single actuator configured to direct movement of the distal tip of the medical device in at least two directions via rotational movement of the single actuator about a first axis and a second axis;
   an elongate body having a longitudinal axis, the elongate body moveably coupled to the single actuator via a shaft and configured to permit rotational movement of the single actuator relative to the body about the first axis and the second axis, wherein a longitudinal axis of the shaft defines the first axis or the second axis;
   wherein rotation of the single actuator about the first axis tensions a first elongate control member to direct the distal tip of the medical device up or down, wherein rotation of the single actuator about the second axis tensions a second elongate control member independent of tensioning the first elongate control member to direct the distal tip of the medical device left or right, and wherein a proximal end of the first elongate control member or the second elongate control member is attached to the single actuator; and
   a rail having an elongate member, wherein the elongate member has a longitudinal axis fixedly positioned parallel to the longitudinal axis of the elongate body and, simultaneously, the rail is moveably coupled to the single actuator to permit movement of the single actuator relative to the elongate member to direct corresponding movement of the distal tip of the medical device.

2. The control of claim 1, wherein at least one of the first elongate control member or the second elongate control member is attached to a plate coupled to the shaft.

3. The control of claim 1, wherein the single actuator is rotatable about the longitudinal axis of the elongate member of the rail to direct rotational movement of the distal tip of the medical device about a longitudinal axis of the medical device.

4. The control of claim 1, wherein at least one of the first elongate control member and the second elongate control member includes a cable at least partially disposed within a sheath.

5. A system for orienting a medical device having a longitudinal axis and elongate control members operably associated with a distal tip of the medical device, the system comprising:
   a control including:
      a handle operably associated with at least two elongate control members and configured to direct movement of the distal tip of the medical device in at least two directions via rotational movement of the handle about a first axis and a second axis, respectively;
      a body moveably coupled to the handle via a shaft, the body configured to permit rotational movement of the handle relative to the body, wherein rotation of the handle about the first axis directs the distal tip of the medical device up or down, and rotation of the handle about the second axis directs the distal tip of the medical device left or right, wherein a longitudinal axis of the shaft defines the first axis or the second axis, and wherein each of the first axis and the second axis is transverse to a longitudinal axis of the body; and
   a frame located external to the body and configured to be fixedly mounted relative to a patient, the frame moveably coupled to the body and configured to permit rotational movement of the handle and the body relative to the patient about a third axis while the frame remains stationary relative to the patient, wherein rotation of the handle and the body relative to the frame and about the third axis directs rotation of the distal tip of the medical device about the longitudinal axis of the medical device.

6. The system of claim 5, wherein the frame includes a rail configured to permit rotational movement of the handle and the body about a longitudinal axis of the rail to direct rotation of the distal tip of the medical device.

7. The system of claim 5, wherein the frame includes a rail configured to permit longitudinal movement of the handle and the body along the rail to direct the distal tip of the medical device generally forward or backward.

8. The system of claim 5, wherein at least one of the elongate control members includes a cable having a proximal end fixedly attached to the handle.

9. The system of claim 5, wherein the system includes an endoscope.

10. The system of claim 5, wherein the at least two elongate control members include four elongate control members each having a proximal end and a distal end, wherein the proximal ends of two of the elongate control members are attached to the handle, and the proximal ends of two of the elongate control members are attached to an element coupled to the shaft.

11. A surgical system, comprising:
a first control for controlling a distal region of a first medical device having at least two first elongate control members operably associated with the distal region of the first medical device, comprising:
a first actuator operably associated with the at least two first elongate control members and configured to direct movement of the distal region of the first medical device in at least up, down, left, and right directions via movement of the at least two first elongate control members, wherein a proximal end of at least one of the first elongate control members is attached to the first actuator;
a first body moveably coupled to the first actuator via a shaft, the first body configured to permit movement of the first actuator in at least three directions relative to the first body to actuate the movement of the distal region of the first medical device, wherein the at least three directions include a first rotation of the first actuator about a first axis defined by the shaft to tension one of the at least two first elongate control members for moving the distal region of the first medical device up or down, and a second rotation of the first actuator and the shaft about a second axis orthogonal to the shaft to tension another one of the at least two first elongate control members for moving the distal region of the first medical device left or right, and wherein the first body is moveably coupled to a first rail, and the first body and the first rail have longitudinal axes permanently fixed parallel to each other; and
a second control for controlling a distal region of a second medical device having at least two second elongate control members operably associated with the distal region of the second medical device, the second control comprising:
a second actuator operably associated with the at least two second elongate control members and configured to direct movement of the distal region of the second medical device in at least up, down, left, and right directions via movement of the at least two second elongate control members; and
a second body moveably coupled to the second actuator and configured to permit movement of the second actuator in at least three directions relative to the second body to actuate the movement of the distal region of the second medical device in the at least up, down, left, and right directions.

12. The surgical system of claim 11, wherein the first and second rails are coupled to a frame fixedly mounted to an operating table.

13. The surgical system of claim 11, wherein at least one of the first rail and the second rail is configured to permit longitudinal movement of the corresponding first actuator or second actuator to direct the distal tip of the corresponding first medical device or second medical device generally forward or backward.

14. The surgical system of claim 11, wherein at least one of the first rail and the second rail is configured to permit rotational movement of the corresponding first actuator or second actuator to direct rotational movement of the distal tip of the corresponding first medical device or second medical device.

15. The surgical system of claim 11, wherein the first actuator is positioned for use by a left hand of a user and the second actuator is positioned for use by a right hand of the user.

16. The surgical system of claim 11, further comprising the first medical device and the second medical device.

17. The surgical system of claim 16, wherein at least one of the first medical device and the second medical device includes an instrument for performing an examination or procedure on a patient.

18. The surgical system of claim 16, wherein at least one of the first medical device and the second medical devices includes a catheter having one or more lumens for receiving an instrument.

19. The surgical system of claim 11, wherein at least one of the first elongate control members includes a cable disposed within a sheath, a distal end of the sheath abutting a wall of the first body.

20. The surgical system of claim 11, further including an endoscope.

21. The control system of claim 1, wherein the first axis, the second axis, and the longitudinal axis of the elongate body are generally orthogonal to each other.

22. The control of claim 1, wherein the rail is coupled to the single actuator via a clamp having a lumen that receives the rail.

23. The control of claim 22, wherein the clamp is fixedly coupled to the elongate body.

24. The system of claim 5, wherein the shaft is fixedly coupled to a plate, and wherein a proximal end of at least one of the elongate control members is attached to the plate.

25. The system of claim 6, wherein the longitudinal axis of the rail is parallel to the longitudinal axis of the body.

26. The control of claim 2, wherein the plate includes a groove that receives the other of the first elongate control member or the second elongate control member.

27. The control of claim 4, wherein a distal end of the sheath abuts a wall of the elongate body.

* * * * *